(12) United States Patent
Barakat et al.

(10) Patent No.: US 11,172,885 B2
(45) Date of Patent: Nov. 16, 2021

(54) MEDICAL DEVICE EQUIPPED WITH SENSORS

(71) Applicants: CENTRE NATIONAL DE LA RECHERCHE SCIENTIFIQUE, Paris (FR); ECOLE POLYTECHNIQUE, Palaiseau (FR); ECOLE NORMALE SUPERIEURE DE CACHAN, Cachan (FR)

(72) Inventors: Abdul Barakat, Gif-sur-Yvette (FR); Franz Bozsak, Bourg-la-Reine (FR); Yvan Eric Bonnassieux, Paris (FR); Bruno Le Pioufle, Paris (FR); Olivier Francais, Melun (FR); Bruno Carreel, Paris (FR)

(73) Assignees: Centre National de la Recherche Scientifique, Paris (FR); Ecole Polytechnique, Paris (FR); Ecole Normale Superieure de Cachan, Cachan (FR)

( * ) Notice: Subject to any disclaimer, the term of this patent is extended or adjusted under 35 U.S.C. 154(b) by 407 days.

(21) Appl. No.: 15/516,531

(22) PCT Filed: Oct. 2, 2015

(86) PCT No.: PCT/EP2015/072859
§ 371 (c)(1),
(2) Date: Apr. 3, 2017

(87) PCT Pub. No.: WO2016/050972
PCT Pub. Date: Apr. 7, 2016

(65) Prior Publication Data
US 2018/0235545 A1    Aug. 23, 2018

(30) Foreign Application Priority Data

Oct. 3, 2014 (FR) .................................. 1459531

(51) Int. Cl.
  *A61B 5/00* (2006.01)
  *A61B 5/0538* (2021.01)
  *A61F 2/82* (2013.01)

(52) U.S. Cl.
  CPC .......... *A61B 5/6862* (2013.01); *A61B 5/0031* (2013.01); *A61B 5/0538* (2013.01);
  (Continued)

(58) Field of Classification Search
  CPC ........................... A61B 5/6862; A61B 5/0031
  See application file for complete search history.

(56) References Cited

U.S. PATENT DOCUMENTS 5,800,350 A    9/1998 Coppleson et al.
5,938,624 A    8/1999 Akerfeldt et al.
(Continued)

FOREIGN PATENT DOCUMENTS

CA    2814557 A1    4/2012
CN    1329290 A    1/2002
(Continued)

OTHER PUBLICATIONS

U.S. Appl. No. 16/091,766, filed Oct. 5, 2018, Bozsak et al.
(Continued)

*Primary Examiner* — Daniel L Cerioni
*Assistant Examiner* — Yasmeen S Warsi
(74) *Attorney, Agent, or Firm* — Wolf, Greenfield & Sacks, P.C.

(57) ABSTRACT

A medical device including an electric measurement circuit, in which are connected at least two sensors the impedance of which varies as a function of a sensed physical parameter, a source of electrical power for powering the electric measurement circuit, an antenna for emitting an electromagnetic field as a function of the impedance of the electric measurement circuit, each of the sensors being associated with a (Continued)

switch for short circuiting the sensor in the measurement circuit, the medical device further including a system for controlling the switches in order successively to command the opening or closing of the switches in determined configurations. The medical device may notably be able to be applied to the human body or implanted in the human body.

34 Claims, 3 Drawing Sheets

(52) U.S. Cl.
CPC ............ *A61B 5/4851* (2013.01); *A61B 5/686* (2013.01); *A61B 5/7225* (2013.01); *A61B 2560/0219* (2013.01); *A61B 2562/028* (2013.01); *A61B 2562/0247* (2013.01); *A61B 2562/0261* (2013.01); *A61B 2562/0271* (2013.01); *A61F 2/82* (2013.01)

(56) References Cited

U.S. PATENT DOCUMENTS

| | | | |
|---|---|---|---|
| 6,063,028 A | 5/2000 | Luciano | |
| 6,090,052 A | 7/2000 | Akerfeldt et al. | |
| 6,106,486 A | 8/2000 | Tenerz et al. | |
| 6,112,598 A | 9/2000 | Tenerz et al. | |
| 6,206,835 B1 | 3/2001 | Spillman, Jr. et al. | |
| 6,428,336 B1 | 8/2002 | Akerfeldt | |
| 6,437,551 B1 | 8/2002 | Krulevitch et al. | |
| 6,461,301 B2 | 10/2002 | Smith | |
| 6,679,269 B2 | 1/2004 | Swanson | |
| 8,233,979 B1* | 7/2012 | Shelchuk | A61N 1/056 607/9 |
| 8,277,386 B2 | 10/2012 | Ahmed et al. | |
| 8,478,378 B2 | 7/2013 | Lal et al. | |
| 8,491,567 B2 | 7/2013 | Magnin et al. | |
| 8,777,898 B2 | 7/2014 | Suon et al. | |
| 8,840,560 B2 | 9/2014 | Hossack et al. | |
| 9,121,806 B2 | 9/2015 | Bhansali et al. | |
| 9,301,699 B2 | 4/2016 | Hubinette et al. | |
| 2002/0043113 A1 | 4/2002 | Tulkki et al. | |
| 2002/0077627 A1 | 6/2002 | Johnson et al. | |
| 2002/0177782 A1 | 11/2002 | Penner | |
| 2004/0127960 A1* | 7/2004 | Mass | A61N 1/37223 607/60 |
| 2005/0065592 A1 | 3/2005 | Holzer | |
| 2006/0047205 A1 | 3/2006 | Ludomirsky et al. | |
| 2006/0254600 A1 | 11/2006 | Danek et al. | |
| 2007/0255145 A1 | 11/2007 | Smith et al. | |
| 2007/0255270 A1 | 11/2007 | Carney | |
| 2008/0262489 A1 | 10/2008 | Steinke | |
| 2009/0118808 A1* | 5/2009 | Belacazar | A61N 1/05 607/122 |
| 2010/0191141 A1 | 7/2010 | Aberg | |
| 2011/0054583 A1 | 3/2011 | Litt et al. | |
| 2011/0251469 A1 | 10/2011 | Varadan | |
| 2012/0016206 A1 | 1/2012 | Ramarajan et al. | |
| 2012/0036689 A1 | 2/2012 | Sjosten et al. | |
| 2012/0061257 A1 | 3/2012 | Yu et al. | |
| 2012/0172731 A1 | 7/2012 | Smith | |
| 2012/0190989 A1 | 7/2012 | Kaiser et al. | |
| 2012/0316454 A1 | 12/2012 | Carter | |
| 2013/0274712 A1 | 10/2013 | Schecter | |
| 2013/0282084 A1 | 10/2013 | Mathur et al. | |
| 2014/0005558 A1 | 1/2014 | Gregorich | |
| 2014/0058197 A1 | 2/2014 | Salahieh et al. | |
| 2014/0058275 A1 | 2/2014 | Gregorich et al. | |
| 2014/0066790 A1 | 3/2014 | Burkett et al. | |
| 2014/0066791 A1 | 3/2014 | Burkett | |
| 2014/0081244 A1 | 3/2014 | Voeller et al. | |
| 2014/0180031 A1 | 6/2014 | Anderson | |
| 2014/0276109 A1 | 9/2014 | Gregorich | |
| 2014/0276223 A1 | 9/2014 | Gustafsson | |
| 2014/0284422 A1 | 9/2014 | Sapir | |
| 2014/0343382 A1 | 11/2014 | Kersey et al. | |
| 2015/0032011 A1 | 1/2015 | McGowan et al. | |
| 2015/0051499 A1 | 2/2015 | McGowan | |
| 2015/0209526 A1 | 7/2015 | Matsubara et al. | |
| 2015/0297807 A1 | 10/2015 | Leblanc et al. | |
| 2015/0313478 A1 | 11/2015 | Veszelei et al. | |
| 2016/0051323 A1 | 2/2016 | Stigall et al. | |
| 2016/0058382 A1 | 3/2016 | Burkett et al. | |
| 2016/0058977 A1 | 3/2016 | Burkett et al. | |
| 2016/0073957 A1 | 3/2016 | Szunyog | |
| 2016/0121085 A1 | 5/2016 | Burkett et al. | |
| 2016/0287178 A1 | 10/2016 | Ranganathan et al. | |
| 2016/0303354 A1 | 10/2016 | Burkett et al. | |
| 2019/0159684 A1 | 5/2019 | Bozsak et al. | |

FOREIGN PATENT DOCUMENTS

| | | |
|---|---|---|
| CN | 1576862 A | 2/2005 |
| CN | 1788677 A | 6/2006 |
| CN | 101004424 A | 7/2007 |
| CN | 102370476 A | 3/2012 |
| CN | 102481110 A | 5/2012 |
| DE | 101 03 503 A1 | 8/2002 |
| DE | 10103503 A | 8/2002 |
| EP | 2 271 933 B1 | 12/2012 |
| JP | 2000-271101 A | 10/2000 |
| JP | 2003-532440 A | 11/2003 |
| JP | 2004-41724 A | 2/2004 |
| JP | 2008-526293 A | 7/2008 |
| JP | 2011-513038 A | 4/2011 |
| JP | 2013-502278 A | 1/2013 |
| JP | 2013-510374 A | 3/2013 |
| JP | 2013-539692 A | 10/2013 |
| WO | 99/042176 A1 | 8/1999 |
| WO | WO 00/56210 A1 | 9/2000 |
| WO | 01/037726 A1 | 5/2001 |
| WO | WO 03/057011 A2 | 7/2003 |
| WO | WO 2006/070369 A2 | 7/2006 |
| WO | WO 2006/113747 A2 | 10/2006 |
| WO | WO 2009/103156 A1 | 8/2009 |
| WO | WO 2009/114689 A1 | 9/2009 |
| WO | 2009/136167 A1 | 11/2009 |
| WO | WO 2009/136157 A2 | 11/2009 |
| WO | WO 2011/022418 A2 | 2/2011 |
| WO | WO 2011/057024 A2 | 5/2011 |
| WO | 2011/121581 A1 | 10/2011 |
| WO | WO 2016/050972 A1 | 4/2016 |

OTHER PUBLICATIONS

FR 1560174, Oct. 23, 2015, Written Opinion on Patentability.
FR 1560174, Jun. 17, 2016, Preliminary Search Report.
PCT/EP2016/075456, Dec. 9, 2016, International Search Report and Written Opinion.
PCT/EP2016/075456, May 3, 2018, International Preliminary Report on Patentability.
PCT/EP2017/079960, Apr. 5, 2018, International Search Report and Written Opinion.
PCT/IB2017/001230, Apr. 5, 2018, Internatioanl Search Report and Written Opinion.
FR 1459531, Oct. 3, 2014, Written Opinion on Patentability.
FR 1459531, Jun. 30, 2015, Preliminary Search Report.
PCT/EP2015/072859, Dec. 3, 2015, International Search Report and Written Opinion.
PCT/EP2015/072859, Apr. 13, 2017, International Preliminary Report on Patentability.
PCT/EP2017/058169, Jun. 2, 2017, International Search Report and Written Opinion.
Written Opinion on Patentability for French Application No. 1560174 dated Oct. 23, 2015.
Preliminary Search Report for French Application No. 1560174 dated Jun. 17, 2016.
International Search Report and Written Opinion for International Application No. PCT/EP2016/075456 dated Dec. 9, 2016.

(56) References Cited

OTHER PUBLICATIONS

International Preliminary Report on Patentability for International Application No. PCT/EP2016/075456 dated May 3, 2018.
International Search Report and Written Opinion for International Application No. PCT/EP2017/079960 dated Apr. 5, 2018.
International Search Report and Written Opinion for International Application No. PCT/IB2017/001230 dated May 4, 2018.
Bilge et al., Label-Free Recognition of Drug Resistance via Impedimetric Screening of Breast Cancer Cells. Plos One. 2013;8(3).
Nguyen et al., A cell impedance sensor chip for cancer cells detection with single cell resolution. 2013 IEEE Sensors. Nov. 3, 2013. 1-4.
Srinivasaraghavan et al., Microelectrode bioimpedance analysis distinguishes basal and claudin-low subtypes of triple negative breast cancer cells. Biomedical Microdevices. 2015;17(4):1-11.
Xu et al., A review of impedance measurements of whole cells. Biosensors and Bioelectronics. Oct. 22, 2015. Volume 77. 824-836.
Arndt et al., Bioelectrical impedance assay to monitor changes in cell shape during apoptosis. Biosensors and Bioelectronics. 2004;19:583-94.
Brug et al., The Analysis of Electrode Impedances Complicated by the Presence of a Constant Phase Element. Journal of Electroanalytical Chemistry and Interfacial Electrochemistry. 1984;176:275-95.
Chauveau et al., Ex Vivo Discrimination between Normal and Pathological Tissues in Human Breast Surgical Biopsies Using Bioimpedance Spectroscopy. Annals of the New York Academy of Sciences. 1999;873:42-50.
Cho et al., Chip-based time-continuous monitoring of toxic effects on stem cell differentiation. Annals of Anatomy. 2009;191:145-52.
Cho et al., Electrical characterization of human mesenchymal stem cell growth on microelectrode. Microelectronic Engineering. Science Direct. 2008;85:1272-4.
Cho et al., Impedance monitoring of herpes simplex virus-induced cytopathic effect in Vero cells. Elsevier. Sensors and Actuators B. 2007;123:978-82.
Cole et al., Dispersion and Absorption in Dielectrics. Journal of Chemical Physics. 1941;9:341-51.
Franks et al., Impedance Characterization and Modeling of Electrodes for Biomedical Applications. Biomedical Engineering. IEEE Transactions on Biomedical Engineering. 2005;52(7):1295-1302.
Giaever et al., A morphological biosensor for mammalian cells. Nature. 1993;366:591-2.
Giaever et al., Micromotion of mammalian cells measured electrically. Proceedings of the National Academy of Sciences. 1991;88:7896-900.
Grimnes et al., Bioimpedance and Bioelectricity Basics. Academic. Elsevier. Second Edition. 2000. 484 pages.
Helen et al., Investigation of tissue bioimpedance using a macroneedle with a potential application in determination of needle-to-nerve proximity. Proceedings of the 8th International Conference on Sensing Technology. Sep. 2-4, 2014. 376-80.
Hilderbrandt et al., Detection of the osteogenic differentiation of mesenchymal stem cells in 2D and 3D cultures by electrochemical impedance spectroscopy. Journal of Biotechnology. 2010;148:83-90.
Hirschorn et al., Determination of effective capacitance and film thickness from constant-phase-element parameters. Electrochimica Acta. 2010;55:6218-27.
Linderholm et al., Two-dimensional impedance imaging of cell migration and epithelial stratification. Lab on a Chip. Paper. 2006;6:1155-62.
Luong et al., Monitoring Motility, Spreading, and Mortality of Adherent Insect Cells Using an Impedance Sensor. Analytical Chemistry. 2001;73:1844-8.
Orazem et al., Dielectric Properties of Materials Showing Constant-Phase-Element (CPE) Impedance Response. Journal of the Electrochemcial Society. 2013;160(6):C215-C225.
Orazem et al., Electrochemical Impedance Spectroscopy. John Wiley & Sons, Inc. 2008. 533 pages.
Pauly et al., Electrical Properties of Mitochondrial Membranes. The Journal of Biophysical and Biochemical Cytology. 1960;7(4):589-601.
Qiao et al., Bioimpedance Analysis for the Characterization of Breast Cancer Cells in Suspension. Biomedical Engineering. IEEE Transactions. 2012;59:2321-90.
Rigaud et al., In vitro tissue characterization and modelling using electrical impedance measurements in the 100 Hz-10 MHz frequency range. Physiological Measurement. 1995;16:A15-A28.
Schade-Kampmann et al., On-chip non-invasive and label-free cell discrimination by impedance spectroscopy. Cell Prolif. 2008;41:830. 40.
Xiao et al., Assessment of Cytotoxicity Using Electric Cell-Substrate Impedance Sensing: Concentration and Time Response Function Approach. Analytical Chemistry. 2002;74:5748-53.
Dec. 3, 2015 International Search Report issued in International Patent Application No. PCT/EP2015/072859.
Written Opinion on Patentability for French Application No. 1459531 dated Oct. 3, 2014.
Preliminary Search Report for French Application No. 1459531 dated Jun. 30, 2015.
International Search Report and Written Opinion for International Application No. PCT/EP2015/072859 dated Dec. 3, 2015.
International Preliminary Report on Patentability for International Application No. PCT/EP2015/072859 dated Apr. 13, 2017.
International Search Report and Written Opinion for International Application No. PCT/EP2017/058169 dated Jun. 21, 2017.
[No Author Listed], Electronique et informatique. Daniel Robert. http://www.electronique-et-informatique.fr/anglais/Digit/Digit_8T.html Sep. 22, 2006. Last accessed Aug. 7, 2018. 9 pages.
[No Author Listed], Ring oscillator. https://en.wikipedia.org/w/index.php?title=Ring_oscillator&oldid=674008095 Aug. 1, 2015. Last accessed Aug. 7, 2018. 4 pages.
European Communication for European Application No. 15771665.5 dated Feb. 5, 2020.
EP 15771665.5, Feb. 2, 2020, European Communication.

* cited by examiner

MEDICAL DEVICE EQUIPPED WITH SENSORS

RELATED APPLICATIONS

This application is a national stage filing under 35 U.S.C. § 371 of international PCT application PCT/EP2015/072859, filed Oct. 2, 2015, which claims foreign priority benefit under 35 U.S.C. § 119(a)-(d) or 35 U.S.C. § 365(b) of French application number 1459531, filed Oct. 3, 2014.

The present invention relates to a medical device equipped with sensors. The invention is also aimed at a medical system comprising such a medical device and at a method for interrogating such a medical device, notably in a medical system.

The invention is notably aimed at an implantable medical device such as a stent (sometimes also known as an "arterial endoprosthesis", a "vascular stent" or sometimes even simply a "spring") equipped with sensors.

A stent is a device of tubular shape created by a deformable mesh, notably made of metal or of a biodegradable polymer. The stent is introduced into the body of a patient in a furled state, with the meshes closed, and is then expanded inside the patient's body, for example using angioplasty which causes the meshes to unfurl. The unfurled stent allows a cavity in the patient's body to be held open. It is known that fitting a stent may notably cause inflammation of the tissue, hyperplasia and/or blood clotting.

As a consequence, a stent may be equipped with sensors which make it possible to monitor the state of the tissue around the stent in order, if appropriate, to adapt the patient's treatment accordingly. Sensors may also be provided to make sure that the stent is performing its function of holding a cavity open.

It is known practice to interrogate a stent, which means to say to gather information originating from this stent, using a contactless interrogation device kept outside the patient. In general, such a contactless interrogation device is configured to measure an electromagnetic field emitted by the stent implanted in the patient.

Patent EP-B-2 271 933 thus describes a method for characterizing cells in the vicinity of a medical device implanted in a patient, notably a stent, by measurements of impedance at different frequencies.

Application WO-A-2009/1 361 677 describes an implantable medical device such as a stent that has an electrically conducting surface and an impedance sensor for measuring the impedance of the conducting surface of the implantable medical device, at different frequencies, by using the conducting surface as an electrode. The measurements taken are used to determine the degree of restenosis of the tissues in the region of the implantable device, namely the thickness of tissue that has grown at the conducting surface of the implantable medical device.

These documents teach methods providing overall information about the implantable device, without making it possible to obtain independently the measurements taken by each sensor with which the implantable medical device is equipped.

Elsewhere, U.S. Pat. No. 8,478,378 discloses a stent equipped with sensors distributed over its internal surface, oriented towards the passage through the stent, or "luminal" surface. The sensors are configured to send a specific characteristic output signal in response to an excitation. The specific characteristic signal may notably be a wavelength specific to each of the sensors. U.S. Pat. No. 8,478,378 indicates that in this way an output signal including signals from all or most of the sensors suggests that a great number of sensors are not covered with a layer of endothelial cells.

Finally, application WO-A-2011/121581 describes an implantable medical device capable of responding to an interrogation electromagnetic field emitted by a remote interrogation device. The implantable medical device is equipped with a plurality of modulators consisting of RFID (Radio-Frequency IDentification) chips. The RFID chips are designed so that the implantable medical device responds to an interrogation electromagnetic field at a modulation that generates a unique respective identification code.

The use of RFID chips as sensors in the medical device does, however, limit the number of sensors with which it may be equipped. This is because increasing the number of RFID chips causes a corresponding increase in the price of the medical device. These RFID chips may also, furthermore, be used only as impedance sensors. Furthermore, according to that document, the medical device needs to be at least partially made of a metallic material having good electrical conductivity. Finally, according to that document, the RFID chips need to be implanted within the actual structure of the implantable medical device, making the creation of the latter a particularly complex matter.

Implantable medical devices are also known from WO-A-01/37 726 or U.S. Pat. No. 6,206,835. These medical devices comprise a structure that can be implanted into the body in order to assist with the performance of a vital function within the body. One or more sensors are associated with this implantable structure, making it possible to measure a parameter associated with the structure. Finally, these medical devices comprise a communication circuit coupled to the sensor(s) so as to deliver a signal that is a function of the measured parameter and so as to transmit this signal to a receiving device, outside the body, in a non-invasive manner.

It is an objective of the invention to alleviate the problems mentioned hereinabove. It is a notable objective of the invention to propose a medical device of simple structure, and therefore limited cost, making it possible to distinguish the parameters measured by various sensors with which the medical device is equipped. In one preferred embodiment, the medical device can be implanted into the body of the patient and is configured to make it possible, without intrusion into the patient's body, to determine whether it is correctly implanted.

The invention proposes a medical device comprising an electric measurement circuit, in which are connected at least two sensors the impedance of which varies as a function of a sensed physical parameter, a source of electrical power for powering the electric measurement circuit, an antenna for emitting an electromagnetic field as a function of the impedance of the electric measurement circuit, each of the sensors being associated with a switch for short circuiting the sensor in said measurement circuit, the medical device further comprising a system for controlling the switches in order successively to command the opening or closing of the switches in determined configurations.

Thus, according to the invention, the medical device is equipped with any type of variable-impedance sensors, the sensors being joined together in a circuit referred to as a measurement circuit. A control system allows the various sensors to be short circuited in predetermined configurations so that the electromagnetic field emitted by the medical device corresponds to the configuration of the measurement circuit. By taking successive measurements, corresponding to linearly independent configurations—for example one sensor short circuited at a time or all the sensors except one short circuited at a time—it is very easily possible to obtain qualitative information about the values measured by each of the sensors of the medical device which are located at known positions on the medical device.

What is meant by "short circuiting a sensor" is creating a circuit configuration such that the current passing through the sensor is zero, it being possible for the other sensors to be supplied with current. In other words, "short circuiting a sensor" here means cutting off the supply of current to this sensor.

For preference, the medical device comprises one or more of the following features, considered alone or in combination:
- the medical device can be implanted in the human body or applied to the human body;
- each switch is formed of one or more transistors, notably one or more field effect transistors FETs, and, more particularly, one or more N-channel or P-channel enhancement or depletion MOSFET field effect transistors with metal oxide gate, one or more MEMSs or one or more mechanical switches;
- the system for controlling the switches comprises a control circuit powered by the electrical power source and preferably configured so as successively to command the opening or closing of the various switches one after the other;
- the control system comprises components implanted directly in the measurement circuit, preferably for successively commanding the opening or closing of the various switches one after the other;
- each assembly of a switch and of a sensor is mounted in series and the assemblies of a switch and of a sensor are mounted in parallel with one another;
- each assembly of a switch and of a sensor is mounted in parallel and the assemblies of a switch and of a sensor are mounted in series with one another;
- the electrical power source comprises a current-conducting surface of the medical device which is designed to induce an electric current under the effect of an electromagnetic field;
- at least one of the sensors is arranged on a surface of the medical device, which surface is intended to be in contact with part of the body to which the device may be applied or in which the device may be implanted;
- the antenna is formed by at least part of the medical device;
- the measurement circuit comprises a plurality of determined impedances, each one associated with a switch the opening and closing of which are commanded by the control system;
- the medical device may be implanted in the human body and chosen from the group comprising:
  - a vascular stent or stent, at least one sensor preferably being arranged on an abluminal surface of the vascular stent,
  - a heart valve,
  - a pacemaker,
  - a cochlear implant,
  - an implant for the throat,
  - an orthopaedic implant, or
  - a tissue-engineered construct;
- each sensor is chosen from:
  - a shear sensor,
  - a pressure sensor,
  - an impedance sensor,
  - a heat dissipation sensor,
  - a strain gauge, and
  - a flow sensor, notably of the hot wire type; and
- the implantable medical device is a vascular stent with at least one impedance sensor arranged on an abluminal surface of the vascular stent.

The invention also relates to a medical system comprising a medical device as described hereinabove in all possible combinations thereof and a unit for receiving information from the medical device, comprising means for sensing the electromagnetic field emitted by the antenna of the medical device.

The medical system may further comprise a unit for interrogating the medical device, preferably coinciding with the information receiving unit, preferably comprising means for emitting an electromagnetic field able to create an induced current in the measurement circuit of the medical device.

The medical system may also comprise a data processing unit for processing the information received by the receiving unit, for example a computer.

The invention also relates to a method for interrogating a medical device as described hereinabove in all combinations thereof, notably in a medical system as described hereinabove in all combinations thereof, comprising the steps of:
- supplying the measurement circuit of the medical device,
- activating the control system so that it successively commands the opening or closing of each of the switches in determined configurations, and
- measuring the electromagnetic field emitted by the antenna of the medical device.

The attached figures will make it easy to understand how the invention may be embodied. In these figures, identical references denote elements that are similar.

In the remainder of the description, elements that are identical or have identical functions bear the same reference sign in all the various embodiments. For the sake of conciseness of the present description, these elements are not described with reference to each of the embodiments, only the differences between embodiments being described.

Figure 1:
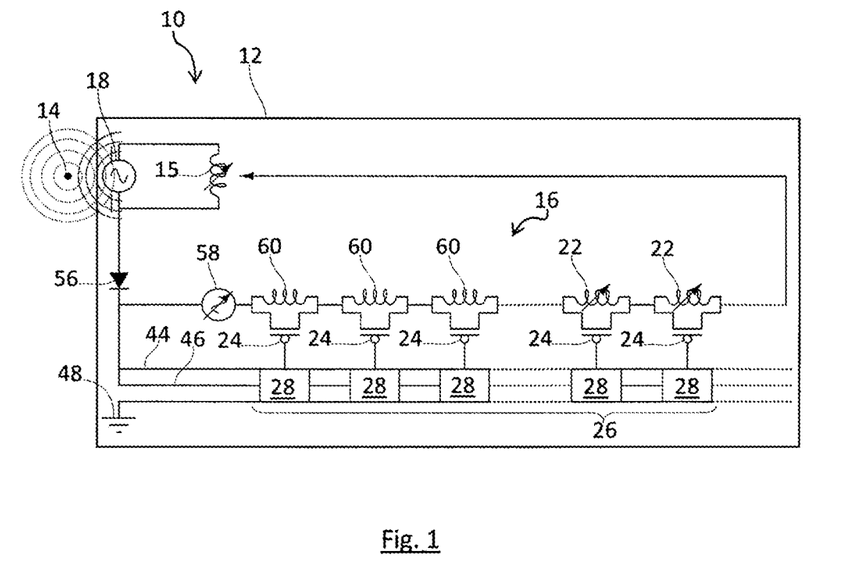
FIG. 1 schematically depicts a first example of a medical system comprising a medical device.

FIG. 1 schematically illustrates a medical system 10 comprising an implantable medical device 12 and a unit 14, in this instance a single unit, for interrogating the medical device 12 and receiving information from this same medical device 12. Of course, the units for interrogating and for receiving information may, as an alternative, be separate. The medical system 10 may further comprise a data processing unit for processing the information received by the receiving unit, for example a computer.

The implantable medical device 12 comprises a variable impedance 15. The magnitude of this variable impedance 15 is controlled by a control unit, not depicted, as a function of the impedance in a measurement circuit 16, notably connecting the various sensors 22 of the implantable medical device. The implantable medical device 12 further comprises an electrical power source, in this instance a source of electric current formed by the body 18 of the implantable medical device 12. Specifically, under the effect of an electromagnetic field emitted by the interrogation unit 14, the body 18 of the implantable medical device 12 induces a current. As an alternative, a separate antenna or armature electrically insulated from the body 18 of the implantable medical device 12 may also be provided, notably in instances in which the implantable medical device 12 is partially or completely unsuited to acting as an armature. In this last case in particular, an electrical power source for the measurement circuit may comprise a current-conducting surface of the implantable medical device, designed to induce an electric current under the effect of an electromagnetic field. An electric battery or cell may also be provided as electrical power source for the implantable medical device 12.

The body 18 of the implantable medical device 12 also acts here as an emitting antenna to emit an electromagnetic field to outside the body in which the implantable medical device is implanted. For example, for a constant strength of current of the electrical power source, the strength of this field is directly dependent on the variable impedance 15, which is a function of the impedance in the measurement circuit 16. Thus, the strength or a norm of the electromagnetic field emitted by the body 18 of the implantable medical device 12 (or, more generally, the emitting antenna) is a function of the impedance of the measurement circuit 16. As an alternative, the implantable medical device 12 may comprise an antenna distinct from the body of the implantable medical device or the antenna may be formed by at least part of the implantable medical device.

The implantable medical device 12 is, for example, a stent. A stent is a tubular metal device, preferably meshed, slipped into a natural human (or animal) cavity in order to hold it open, as described hereinabove in the introduction. The stent may for example be made of metal alloy or of polymer, although other materials are also conceivable.

The implantable medical device 12 is equipped with sensors 22 the impedance of which varies as a function of the physical parameter they are sensing. What is meant here by a physical parameter is any property of the science of nature that may be quantified by measurement or calculation, and the various possible values of which are expressed using any real number or complex number. A physical parameter therefore includes, for example, a length, an electric current, a voltage, an impedance, a concentration in a chemical element or even the presence and/or concentration of a biological or biochemical element.

The sensors 22 are distributed over the surface of the implantable medical device. In the particular case of the stent described here, the sensors 22 may notably be distributed:

only on the "abluminal" surface of the body of the stent, namely the opposite surface to the lumen through the stent, which is the surface intended to be in contact with the wall of the cavity to be held open but not on the luminal surface; or only on the luminal surface but not on the abluminal surface; or on both the luminal and abluminal surfaces; and on the surfaces connecting the luminal and abluminal surfaces.

The sensors may be coated with an active agent, for example for limiting the hyperplasia of the tissues in contact with the implantable medical device, notably when they are positioned on the abluminal surface of a stent or more generally on the exterior surface of an implantable medical device intended to be in contact with the wall of the cavity in which the medical device can be implanted.

It should be noted that even positioning just one sensor, notably a pressure sensor, on the abluminal surface of a stent, or more generally on the exterior surface of an implantable medical device, already provides information relating to incorrect positioning of the stent or of the implantable medical device in the cavity. If the measured pressure is low (i.e. below a threshold pressure), it is probable that the sensor is not in contact with a wall of the cavity, but rather with blood for example. If two or more sensors are positioned on the abluminal or exterior surface, the information may be obtained with greater precision by comparing against one another the values measured by the sensors.

Preferably, the sensors are positioned at those locations of the implantable medical device, notably of a stent, that experience the least deformation when the implantable medical device is being fitted, this being so as to avoid damaging the sensors.

Each of the sensors may notably be chosen from:

a shear sensor, a pressure sensor, an impedance sensor, a heat dissipation sensor, a strain gauge, and a flow sensor, notably of the "hot wire sensor" type.

The sensors 22 are variable impedance sensors, which means to say sensors the impedance of which varies as a function of the amplitude or intensity of the physical parameter sensed. As a result, if the amplitude of the physical parameter sensed by a sensor of the implantable medical device 12 varies, the impedance of this sensor in the measurement circuit 16 varies so that, in the absence of any other variation in the measurement circuit 16, the impedance in the measurement circuit 16 also varies.

As illustrated, each sensor 22 is associated with a switch 24 designed to short circuit the sensor 22 with which it is associated. In this instance, this is achieved by mounting the switch 24 in bypass (or in parallel) with the sensor 22 with which it is associated. The sensors 22 here are mounted in series in the measurement circuit 16. For ease of production and miniaturization reasons, each switch here is produced in the form of a transistor 24, in this instance a silicon MOSFET transistor, more specifically an enhancement N-channel MOSFET (or n-MOS) transistor. In other embodiments, each switch or some switches may be produced using a different type of transistor, notably a FET transistor, a depletion MOSFET transistor, notably a depletion P-channel MOSFET transistor, a MEMS (Microelectromechanical system) or a mechanical switch.

FIG. 1 further illustrates a system 26 for controlling the switches 24, which is designed to command successively the opening or closing of the switches 24 in determined configurations. Here, the control system 26 comprises control modules 28 arranged in series with one another, each control module 28 being designed to command the opening or closing of the switch 24 with which it is associated.

In this particular instance, the control system 26 is configured so that it normally keeps the switches 24 closed and opens them successively then closes them again so that only one single switch 24 is open at any time.

In order to do this, each control module 28 is formed here of a logic circuit, created using transistors 30, 32, 34, 36, 38, a resistor 40 and a capacitor 42. The resistor 40 and the capacitor 42 introduce into the logic circuit a time taken to charge the capacitor 42 and a time taken to discharge this same capacitor 42. During these charging and discharging times, the control module 28 commands the opening of the associated switch 24. The switch 24 is kept closed for the rest of the time, thereby short-circuiting the associated sensor 22.

Figure 2:
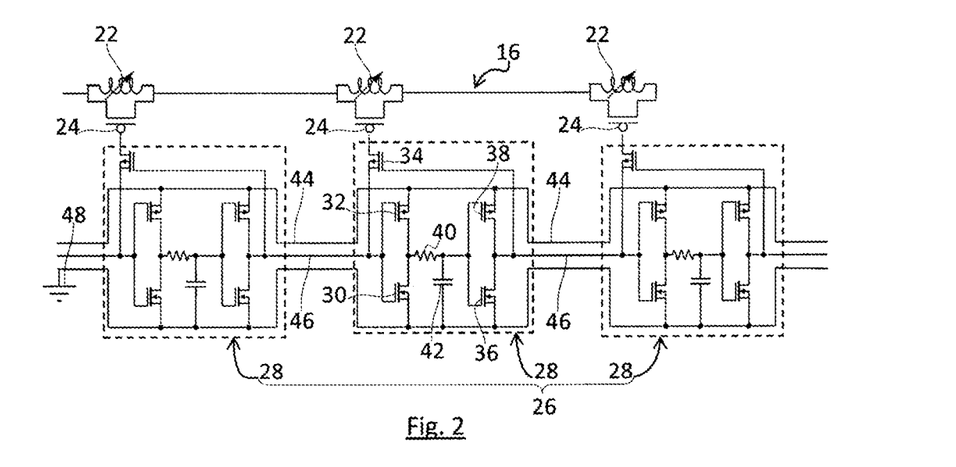
FIG. 2 schematically depicts a detail of the electric circuit of the stent of FIG. 1.

More specifically, and as depicted in FIG. 2, in this instance, each control module 28 is produced using three P-channel transistors 32, 34, 38 and two N-channel transistors 30, 36, as follows (only the connections listed hereinbelow are made):

first and second branches 44, 46 of the measurement circuit 16 are connected in parallel,
the gate of the first transistor 30 and the gate of the second transistor 32 are connected together, and to the source of the third transistor 34 and the second branch 46 of the previous control module 28;
the gate of the fourth transistor 36 and the gate of the fifth transistor 38 are connected together and to a terminal of the resistor 40 and to a terminal of the capacitor 42;
the source of the first transistor 30, the source of the fourth transistor 36 and a terminal of the capacitor 42 are connected to earth 48;
the other terminal of the resistor 40, which is not connected to the capacitor 42, is connected to the drain of the first transistor 30 and to the drain of the second transistor 32;
the drain of the fourth transistor 36 and the drain of the fifth transistor 38 are connected together to the second branch 46 of the next control module 28, as well as the gate of the third transistor 34;
the source of the second transistor 32 and the source of the fifth transistor 38 are connected together to the first branch 44 of the previous control module 28;
the drain of the third transistor 34 is connected to the gate of the transistor 24 that acts as a switch for short circuiting the sensor 22.

Using such a control system, the voltage across the terminals of the measurement circuit 16, which is equal to the sum of the voltages across the terminals of each of the sensors mounted in series in the measurement circuit exhibits successive spikes which are representative of the voltage across the terminals of each of the sensors. To each of the successive spikes, each representative of the voltage across the terminals of a sensor 22, there corresponds a strength of the electromagnetic field emitted by the body 18 of the implantable medical device 12 acting as an emitting antenna.

FIG. 1 shows that there is a rectifier 56 and an AC generator 58 in the implantable medical device 12. These respectively allow the control circuit 26 to be supplied with DC current and allow the measurement circuit 16 to be supplied with a current that has a frequency distinct from, notably lower than, the frequency of the current induced in the antenna 18. This may be useful because the frequency of the induced current is a function of the electromagnetic field emitted by the unit 14, which frequency is preferably chosen so that little of the electromagnetic wave is absorbed by the tissues through which it passes. The use of such a frequency in the measurement circuit may detract from the precision of the measurements taken.

The measurement circuit 16 is also supplemented in FIG. 1 by a combination of assemblies of a fixed and known impedance 60 and of a switch 24, controlled by a control module 28, as is the case with the switches 24 associated with the sensors 22. This combination of known impedances makes it possible to identify the implantable medical device being interrogated, for example by combining a unique and known combination of impedances 60 with each implantable medical device 12. Doing so is of particular benefit in the event that several such implantable medical devices have been implanted in the body of one and the same patient. Certain electromagnetic field spikes measured are therefore used to identify the implantable medical device 12, the other spikes being used to determine the values measured by each of the sensors of the implantable medical device 12 identified. For example, the first electromagnetic field spikes measured may be used to identify the implantable medical device 12 and the subsequent spikes to determine the values measured by each of the sensors of the implantable medical device 12 identified. Furthermore, because these impedances are known, they also allow the medical system 10 to be calibrated. In other words, these known impedances make it possible more precisely to quantify the values measured by the various sensors of the various implantable medical devices.

Figure 3:
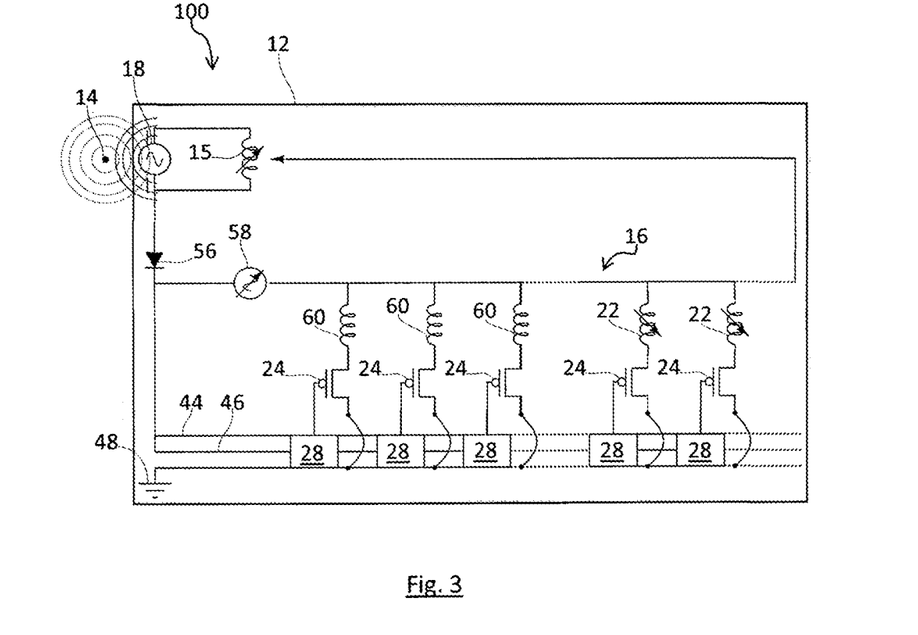
FIG. 3 schematically depicts a second example of a medical system comprising a medical device.

FIG. 3 depicts a second example of a medical system 100. This medical system is substantially identical to the one described previously. However, in this embodiment, in the measurement circuit 16 of the implantable medical device 12, the known impedances 60 and the sensors are mounted in series with the switch 24 associated with them, the assemblies formed of an impedance 60 or of a sensor 22 and of a switch 24 being mounted in parallel (or in bypass) with one another. As a result, because the control modules 28 are identical to those described previously, the electromagnetic field emitted following the creation of an induced current corresponds to the sum of all the impedances 60 and of all the sensors 22 except one, each of the impedances 60 and of the sensors 22 being short circuited in turn.

As an alternative of course, it is possible to create a control module 28 that operates differently, commanding the closing of the switch 24 for an interval of time only, the switch 24 being open the rest of the time. Such operation may also be obtained by keeping the control module 28 as described previously and replacing the enhancement MOSFET transistors used as switches 24 with depletion MOSFET transistors.

Figure 4:
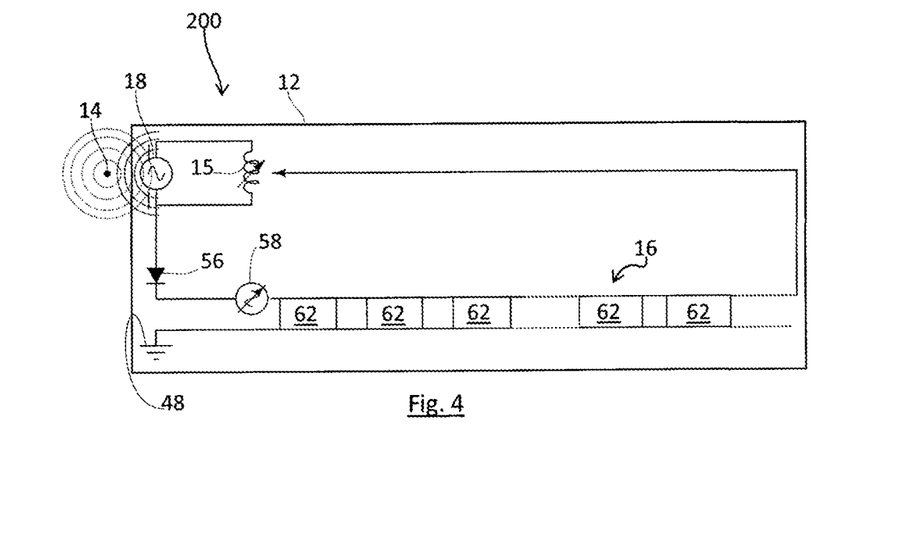
FIG. 4 schematically depicts a third example of a medical system comprising a medical device.
Figure 5:
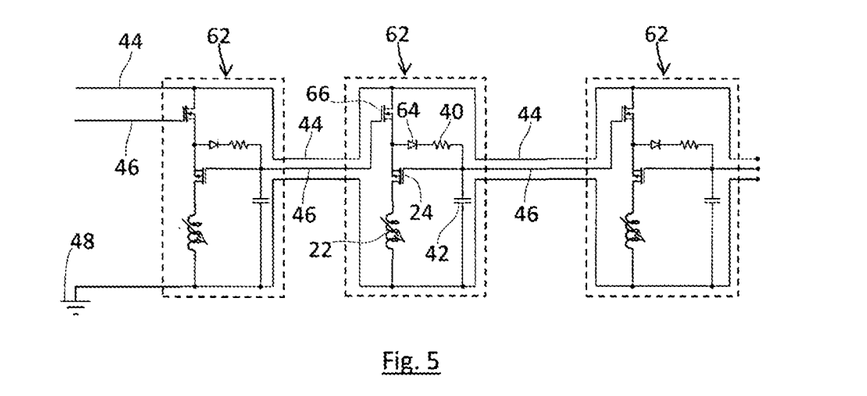
FIG. 5 schematically shows a detail of the medical device of FIG. 4.

FIGS. 4 and 5 illustrate another example of a medical system 200. According to this example, control of the switch 24 that short circuits the sensor 22 or of a known impedance 60 is implanted directly in a module 62 also comprising the known impedance 60 or the sensor 22, and the switch 24, produced here in the form of a transistor. As with the other examples already described, a resistor 40 and a capacitor 42 are used to command the switch 24 in such a way that it short circuits the impedance 60 or the sensor 22 except during an interval of time in which the capacitor 42 is charging.

Here, as depicted in FIG. 5, each module 62 is produced as follows:

the first and second branches 44, 46 are in parallel;
one terminal of the sensor 22 or of the impedance 60 is connected to earth 48;
the other terminal of the sensor 22 or of the impedance 60 is connected to the drain of the transistor 24;
the gate of the second transistor 66 is connected to the second branch 46 of the previous module 62;
the drain of the second transistor 66 is connected to the first branch 44 of the previous and next modules 62;
the source of the second transistor 66 is connected to the source of the transistor 24 and to a diode 64;
the other terminal of the diode 64, which is not connected to the transistors 24, 66, is connected to one terminal of a fixed impedance 40;

the other terminal of the impedance 40, which is not connected to the diode 64, is connected to the gate of the transistor 24, to one terminal of a capacitor 42 connected by its other terminal to earth 48, and to the second branch 46 of the next module 62.

Like with the previous examples, because of the configuration of the modules 62, each sensor 22 and impedance 66 is connected in turn to the antenna 18 so as to be powered, the other sensors 22 and impedances 66 on the other hand being short circuited.

Figure 6:
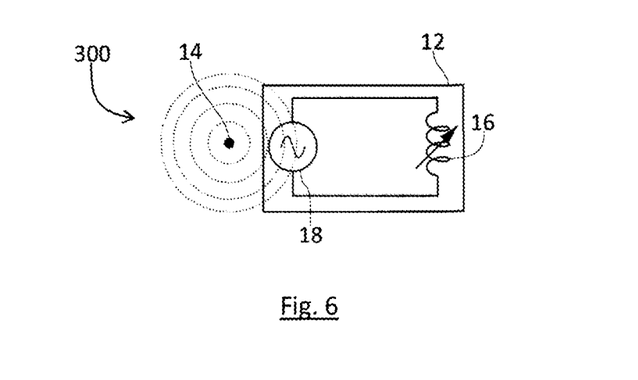
FIG. 6 schematically depicts a fourth example of a medical system comprising a medical device.

Finally, FIG. 6 depicts a fourth exemplary embodiment of a medical system 300. This medical system 300 differs from the previous embodiment 200 in that the measurement circuit 16 is directly connected to the antenna 18 for emitting an electromagnetic field, without the intermediary of a distinct variable impedance (the measurement circuit 16 itself having a variable impedance) and of a control unit for controlling this variable impedance as a function of the impedance of the measurement circuit 16. Therefore the electrical circuit on the medical device 12 is particularly simplified.

It is of course possible to conceive of a structure in which the measurement circuit 16 is connected directly to the antenna, the implantable medical device also comprising a control circuit associated with this measurement circuit and as described for example with reference to FIGS. 2 and 3.

In practice, in the embodiments described previously, each module may notably be produced in the following form. Two measurement electrodes, for example measuring 60×60 µm² made of an electrically conducting material, for example a polymer material or a metallic alloy, preferably biocompatible, are applied to an electrically insulating biocompatible polymer substrate (for example parylene). Electrical components of the control system and the switch are implanted in the polymer substrate.

The medical systems described hereinabove make it possible to carry out a method of interrogating the implantable medical device 12.

This method involves a first step consisting in powering the measurement circuit 16. For preference, this supply of power is achieved using a current induced in an antenna or in the body of the implantable medical device 12 when the latter is configured to generate an induced current. This means that the measurement circuit 16 can be powered only when a measurement is being taken.

The method continues with a step involving activating the control system of the implantable medical device so that it successively commands the opening or closing of each of the switches of the implantable medical device in determined configurations. It should be noted here that, in the context of the examples described with reference to the figures, this activation is performed simultaneously with the powering of the measurement circuit 16, by induction, in response to the emission of an electromagnetic field by the interrogation device.

The method then continues with a step involving measuring the electromagnetic field emitted by the antenna of the implantable medical device. This measurement is performed for a long enough length of time that the control system has had time to command a fairly high number of different configurations of the measurement circuit so that the measurement will make it possible to determine the value measured by each of the sensors 22 of the implantable medical device 12. Throughout the measurement step, the antenna 14 preferably emits a constant electromagnetic field so as to keep the measurement circuit 16 powered and the control system 26 activated.

For preference, each configuration corresponds to the case in which all the sensors or impedances of the measurement circuit are short circuited except for one. Thus, on the basis of the electromagnetic field measured, it is possible to determine first of all which implantable medical device has responded to the interrogation. This is because the first spikes measured in the electromagnetic field emitted by the antenna correspond to fixed impedances, the combination of which makes it possible to identify the implantable medical device. These measured magnetic fields may also make it possible to calibrate the system because the measured magnetic fields correspond to known impedances of the measurement circuit. Finally, the subsequent magnetic fields make it possible to determine the values measured by each of the sensors distributed over the implantable medical device.

A processing unit may be used to determine the value measured by each sensor and the implantable medical device that has responded to the interrogation, notably if the commanded configurations of the measurement circuit are more complex.

In order to do this, the processing unit may notably be designed to carry out Fourrier analyses on the measured signals of electromagnetic field emitted by the antenna of the implantable medical device, to compare the received (and possibly processed) signals against previously measured signals and from this deduce the values measured by the various sensors of the implantable medical device, it being possible for a location to be determined for each of the measured values.

It should be noted here that the method described may be carried out with any type of sensor the impedance of which varies as a function of the physical parameter it is detecting. It should also be noted that the sensors distributed over the implantable medical device may be of different kinds, namely may sense different physical parameters.

The method described hereinabove may notably be carried out in order to determine whether the implantable medical device has been implanted (which means to say positioned) correctly in the natural cavity it is supposed to hold open, and notably whether it really is in contact with the wall of the cavity. Indeed, the effectiveness of a stent, for example, although the same is true for most implantable medical devices, is markedly reduced if it is not pressing against the wall of the cavity (notably of the vein or of the artery) into which it is introduced.

For example, by placing pressure sensors on the abluminal surface of the stent, namely on the opposite surface to the lumen through the stent, the surface that is intended to be in contact with the wall of the cavity in which the implantable medical device is housed, the method described previously therefore makes it possible to determine whether each of these sensors is in contact with the wall, because it makes it possible to determine the pressure measured by each of the sensors. Of course, this function of determining the correct positioning of the stent may be combined, which means to say that sensors, for example pressure sensors, may be arranged on the abluminal surface of the stent and sensors, possibly sensing some other physical parameter, may be arranged on the luminal surface of the stent.

As an alternative, sensors of the same physical parameter are distributed over the abluminal surface and over the luminal surface, substantially at the same position on the stent or on the implantable medical device. In other words, sensors of one and the same physical parameter are arranged at the same point on the stent, on each side of the body of the stent. Comparing the values measured by each of the stent pairs also provides clues as to an incorrect positioning of the stent in the cavity. In particular, if the sensor on the abluminal surface, which ought therefore to be in contact with a wall, is measuring a substantially identical value to the sensor on the luminal surface, which is in contact with the blood, then it is probable that the sensor on the abluminal surface is in fact in contact with blood also, and not with a wall. It is therefore probable that the stent is incorrectly positioned in the cavity.

Of course, the method described hereinabove may make it possible to obtain numerous other pieces of information.

In particular, it may make it possible to determine whether or not a sensor arranged on the luminal or abluminal surface of the stent or, more generally, on a surface of an implantable medical device, notably on a surface of the implantable medical device that is in contact with a wall of the cavity in which the medical device is implanted or on a surface of the implantable medical device intended to be in contact with the blood is covered with endothelial tissue or smooth muscle tissue.

It may also make it possible to determine the make up of the tissue covering the sensors distributed over the implantable medical device (notably over the luminal surface or over the abluminal surface of a stent), for example using electrical impedance spectroscopy (EIS), notably by applying currents of distinct frequencies in the measurement circuit.

The invention is not restricted only to the exemplary embodiments described hereinabove with reference to the figures by way of illustrative and nonlimiting examples.

In particular, the implantable medical device may be chosen from the group comprising:
a heart valve,
a pacemaker,
a cochlear implant,
an implant for the throat,
an orthopaedic implant, or
a tissue-engineered construct.

As an alternative, it is possible for the medical device not to be implantable. It may then notably be something that can be applied to part of the human body. The medical device may in this case take the form of a dressing, a bandage or a tape to be applied to the patient's skin. The medical device may also take the form of a contact lens to be placed over the cornea of a patient.

Finally, according to another alternative form, it is possible for the medical device not to be implantable in the human body or able to be applied thereto.

The invention claimed is:

1. A medical device comprising:
an electric measurement circuit comprising:
at least two sensors to sense an impedance that varies as a function of a physical parameter of a living body, the at least two sensors being arranged to sense the impedance at an inserted position of the at least two sensors within the living body, and
at least two switches, each switch of the at least two switches being associated with a sensor of the at least two sensors and arranged to selectively short circuit the associated sensor by connecting or disconnecting a bypass path for the associated sensor;
a source of electrical power to power the electric measurement circuit;
an antenna to emit an electromagnetic field as a function of the impedance of the electric measurement circuit; and
at least one control circuit to control the at least two switches associated with the at least two sensors to open or close at a time one or more switches of the at least two switches to selectively short circuit one or more associated sensors of the at least two sensors at the time, by connecting or disconnecting one or more bypass paths for the one or more associated sensors and thereby connecting or disconnecting the one or more associated sensors in the electric measurement circuit,
wherein the source of electrical power provides, over a time period, a current that passes through the electric measurement circuit, including any sensors connected in the electric measurement circuit, to the antenna, such that the impedance of the electrical measurement circuit varies over the time period as the at least two switches are controlled to successively open or close over the time period.

2. The medical device according to claim 1, in which the medical device is implantable in the living body.

3. The medical device according to claim 1, in which each switch of the electric measurement circuit comprises one or more transistors, or one or more MEMSs, or one or more mechanical switches.

4. The medical device according to claim 1, in which the at least one control circuit comprises one or more components integrated into the electric measurement circuit.

5. The medical device according to claim 1, in which:
the electric measurement circuit comprises a plurality of assemblies, wherein each assembly of the plurality comprises a sensor of the at least two sensors of the electric measurement circuit, an associated switch of the at least two switches of the electric measurement circuit, and an associated bypass path;
in each assembly of the electric measurement circuit, the switch and the sensor of the assembly are mounted in parallel, and the switch is configured to selectively short circuit the sensor by connecting or disconnecting the bypass path; and
the plurality of assemblies of the electric measurement circuit are mounted in series with one another.

6. The medical device according to claim 1, in which the source of electrical power comprises a current-conducting surface of the medical device, the current-conducting surface being arranged to induce the current under an effect of an electromagnetic field.

7. The medical device according to claim 1, in which at least one of the sensors is arranged on an exterior surface of the medical device, the exterior surface being arranged to contact part of the living body when the medical device is inside the living body, the at least one of the sensors being arranged to sense the impedance of the part of the living body.

8. The medical device according to claim 1, in which the antenna is formed by at least part of the medical device.

9. The medical device according to claim 1, in which the electric measurement circuit comprises a plurality of fixed impedances, each fixed impedance being associated with a switch controlled by the at least one control circuit.

10. The medical device according to claim 1, in which the medical device is a medical device selected from the group consisting of:
a vascular stent or stent,
a heart valve,
a pacemaker,
a cochlear implant,
an implant for the throat, an orthopaedic implant, and
a tissue-engineered construct.

11. The medical device according to claim 1, in which each sensor is a sensor selected from the group consisting of:
a shear sensor,
a pressure sensor,
an impedance sensor,
a heat dissipation sensor,
a strain gauge, and
a flow sensor.

12. The medical device according to claim 10, wherein the medical device is a vascular stent and the at least one sensor is at least one impedance sensor of the vascular stent.

13. A system comprising:
a medical device according to claim 1,
a receiver to receive information from the medical device, the receiver comprising means for sensing an electromagnetic field emitted by the antenna of the medical device.

14. The system according to claim 13, further comprising:
an interrogator to interrogate the medical device, the interrogator comprising an emitter that emits an electromagnetic field able to create the current in the electric measurement circuit of the medical device.

15. The system according to claim 13, further comprising:
a data processor to process the information received by the receiver.

16. A method for interrogating a medical device according to claim 1, the method comprising:
supplying electrical power to the electric measurement circuit of the medical device;
activating the at least one control circuit to successively open or close each switch of the at least two switches over the time period; and
measuring an electromagnetic field emitted by the antenna of the medical device.

17. The medical device according to claim 1, in which the at least one control circuit is configured to perform a control operation to successively open or close each switch of the at least two switches over the time period.

18. The medical device according to claim 4, in which the components are configured to successively command an opening or a closing of each switch of the at least two switches over the time period.

19. The system according to claim 14, in which the interrogator interrogates the medical device concurrently with the receiver receiving information from the medical device.

20. The medical device according to claim 1, in which the at least one control circuit comprises:
at least two control modules each arranged to control opening and closing of a corresponding switch of the at least two switches, and
at least one control line connected to one or more control modules of the at least two control modules.

21. The medical device according to claim 20, in which the at least two control modules comprise three or more control modules and the at least two switches comprise three or more switches.

22. The medical device according to claim 20, in which the at least two control modules are arranged to control the at least two switches to, in succession over the time period, arrange one of the at least two switches in an opposite configuration to other switches of the at least two switches for a time of the time period.

23. The medical device according to claim 22, in which each control module of the at least two control modules comprises a logic circuit to control a timing of opening and subsequently closing, or closing and subsequently opening, a corresponding switch for the time in the succession.

24. The medical device according to claim 22, in which the at least one control line is connected to a first of the at least two control modules to initiate the succession.

25. The medical device according to claim 22, in which, at the time, a one sensor associated with the one switch outputs at least one value indicative of an impedance sensed by the one sensor for transmission from the medical device by the antenna.

26. The medical device according to claim 22, wherein the one switch disconnects a bypass path for one sensor associated with the one switch at the time, such that the one sensor is not short circuited and current passes through the one sensor at the time.

27. The medical device according to claim 26, wherein the other switches of the at least two switches connect a bypass path for each other sensor of the at least two sensors at the time, such that each other sensor is short circuited and no current passes through each other sensor at the time.

28. The medical device according to claim 23, wherein each logic circuit comprises at least one resistor and at least one capacitor.

29. The medical device according to claim 23, in which the at least one control line is connected to a first control module of the at least two control modules, and wherein a first logic circuit of the first control module is connected to a second logic circuit of a second control module of the at least two control modules.

30. The medical device according to claim 29, wherein the succession begins at the first control module at a first time and passes to the second control module at a subsequent second time.

31. The medical device according to claim 30, wherein the first time and the subsequent second time are separated by a time delay.

32. The medical device according to claim 31, wherein the time delay is based on a charging time and/or a discharging time of at least one capacitor of the first logic circuit.

33. A medical device comprising:
an electric measurement circuit comprising:
at least two sensors to sense an impedance that varies as a function of a physical parameter of a living body, the at least two sensors being arranged to sense the impedance at an inserted position of the at least two sensors within the living body, and
at least two switches, each switch of the at least two switches being associated with a sensor of the at least two sensors and arranged to selectively short circuit the associated sensor by connecting or disconnecting a bypass path for the associated sensor;
a source of electrical power to power the electric measurement circuit;
an antenna to emit an electromagnetic field as a function of the impedance of the electric measurement circuit; and
at least one control circuit to control the at least two switches associated with the at least two sensors, the at least one control circuit comprising:
at least two control modules each arranged to control, at a time, opening and closing of a corresponding switch of the at least two switches to selectively short circuit one or more associated sensors of the at least two sensors at the time, by connecting or disconnecting one or more bypass paths for the one or more associated sensors, wherein the at least two control modules are arranged to, in succession over a time period, arrange one of the at least two switches in an opposite configuration to other switches of the at least two switches for a time of the time period, wherein each control module of the at least two control modules comprises a logic circuit to control a timing of opening and subsequent closing, or closing and subsequent opening, a corresponding switch for the time in the succession, each logic circuit comprising at least one resistor and at least one capacitor; and at least one control line connected to one or more control modules of the at least two control modules.

34. A medical device comprising:

an electric measurement circuit comprising:

at least two sensors to sense an impedance that varies as a function of a physical parameter of a living body, the at least two sensors being arranged to sense the impedance at an inserted position of the at least two sensors within the living body, and at least two switches, each switch of the at least two switches being associated with a sensor of the at least two sensors and arranged to selectively short circuit the associated sensor by connecting or disconnecting a bypass path for the associated sensor;

a source of electrical power to power the electric measurement circuit;

an antenna to emit an electromagnetic field as a function of the impedance of the electric measurement circuit; and at least one control circuit to control the at least two switches associated with the at least two sensors, the at least one control circuit comprising:

at least two control modules each arranged to control, at a time, opening and closing of a corresponding switch of the at least two switches to selectively short circuit one or more associated sensors of the at least two sensors at the time, by connecting or disconnecting one or more bypass paths for the one or more associated sensors, wherein the at least two control modules are arranged to, in succession over a time period, arrange one of the at least two switches in an opposite configuration to other switches of the at least two switches for a time of the time period, wherein each control module of the at least two control modules comprises a logic circuit to control a timing of opening and subsequent closing, or closing and subsequent opening, a corresponding switch for the time in the succession; and at least one control line connected to one or more control modules of the at least two control modules, wherein the at least one control line is connected to a first control module of the at least two control modules, and wherein a first logic circuit of the first control module is connected to a second logic circuit of a second control module of the at least two control modules.

* * * * *